United States Patent [19]

Oh et al.

[11] Patent Number: 5,609,855
[45] Date of Patent: Mar. 11, 1997

[54] GEL STICK ANTIPERSPIRANT COMPOSITIONS

[75] Inventors: Young S. Oh, Fairfield; Prem S. Juneja; Daniel S. Connor, both of Cincinnati, all of Ohio

[73] Assignee: The Procter & Gamble Company, Cincinnati, Ohio

[21] Appl. No.: 544,741

[22] Filed: Oct. 18, 1995

Related U.S. Application Data

[63] Continuation of Ser. No. 271,535, Jul. 7, 1994, abandoned, which is a continuation of Ser. No. 696,377, May 6, 1991, abandoned, which is a continuation-in-part of Ser. No. 505,807, Apr. 6, 1990, abandoned.

[51] Int. Cl.⁶ .............................. A61K 7/32; A61K 7/34; A61K 7/38
[52] U.S. Cl. ................................ 424/65; 424/66; 424/68; 424/400; 424/401
[58] Field of Search ........................ 424/65, 66, 68, 424/400, 401

[56] References Cited

U.S. PATENT DOCUMENTS

| | | | |
|---|---|---|---|
| 4,154,816 | 5/1979 | Roehl et al. | 424/68 |
| 4,371,645 | 2/1983 | Mahaffey | 525/108 |
| 4,429,140 | 1/1984 | Murai et al. | 549/370 |
| 4,518,582 | 5/1985 | Schamper et al. | 424/66 |
| 4,664,909 | 5/1987 | Marschner | 424/65 |
| 4,720,381 | 1/1988 | Schamper et al. | 424/66 |
| 4,722,835 | 2/1988 | Schamper et al. | 424/66 |
| 4,725,430 | 2/1988 | Schamper et al. | 424/66 |
| 4,743,444 | 5/1988 | McCall | 424/65 |
| 4,781,917 | 11/1988 | Luebbe et al. | 424/65 |
| 4,816,261 | 3/1989 | Luebbe et al. | 424/65 |

FOREIGN PATENT DOCUMENTS

| | | |
|---|---|---|
| 0286522 | 12/1988 | European Pat. Off. . |
| 64-62377 | 3/1989 | Japan . |
| 0267286 | 3/1990 | Japan . |

OTHER PUBLICATIONS

Kreevoy and Taft, *J. Am. Chem. Soc.*, 77:5590–95 (1955).

*Primary Examiner*—Shelley A. Dodson
*Attorney, Agent, or Firm*—David K. Dabbiere; Leonard W. Lewis; William J. Winter

[57] ABSTRACT

Antiperspirant compositions in the form of gel sticks, which provide the user with excellent antiperspirant efficacy while exhibiting good stability, are disclosed. These compositions utilize particular gelling agents which are stable under the acidic conditions required in antiperspirant compositions. Specifically, the compositions have an acidic pH and include an antiperspirant active, a gelling agent which comprises dibenzylidene alditols substituted on the benzene ring with an electron withdrawing group, and a solvent for the gelling agent. Examples of preferred gelling agents include di(meta-fluorobenzylidene) sorbitol and di(meta-chlorobenzylidene) sorbitol. The method of preventing and controlling perspiration wetness using these compositions is also disclosed.

22 Claims, No Drawings

GEL STICK ANTIPERSPIRANT COMPOSITIONS

CROSS REFERENCE TO RELATED APPLICATIONS

This is a continuation of application Ser. No. 08/271,535, filed on Jul. 7, 1994, now abandoned, which is a continuation of application Ser. No. 07/693,377, filed on May 6, 1991, now abandoned, which is a continuation-in-part application of application Ser. No. 07/505,807, filed Apr. 6, 1990, now abandoned.

TECHNICAL FIELD

The present invention relates to antiperspirant compositions in the form of solid gel sticks. These compositions are stable while providing excellent antiperspirant performance to the user.

BACKGROUND OF THE INVENTION

There are three main types of antiperspirant stick formulations: compressed powder sticks, gel sticks, and wax sticks. While each of these formulation types may have advantages in certain usage situations, each also has disadvantages. For example, compressed powder sticks are often brittle and hard, leaving a cosmetically-unacceptable powder on the skin upon application. Wax-based formulations can also yield cosmetically-unacceptable products due to such factors as hardness, greasiness, and stickiness. The opacity of such wax sticks and the residue created by their use may also be aesthetically undesirable.

Gel-based sticks have several advantages over both compressed powder and wax sticks. For example, the gel sticks tend to leave little or no residue or dust on the skin. Gel sticks also provide a vehicle which glides easily over the skin's surface resulting in very easy and comfortable application of the product.

Unfortunately, the formulation of antiperspirant compositions in the form of effective and stable gel sticks is difficult. The inclusion of antiperspirant actives in such compositions results in the final product having an acidic pH. Many of the gelling agents typically used in forming cosmetic gel sticks either do not form effective hard gels or tend to degrade under such acidic conditions. The products sometimes degrade in periods as short as one month or less. For example, dibenzylidene sorbitol (DBS) is a well-known gelling agent. See, for example, U.S. Pat. No. 4,154,816, Roehl et al., issued May 15, 1979; U.S. Pat. No. 4,816,261, Luebbe et al., issued Mar. 28, 1989; and U.S. Pat. No. 4,743,444, McCall, issued May 10, 1988. Unfortunately, when DBS is used as a gelling agent in an acidic environment, such as is required in an antiperspirant product, it tends to degrade rapidly, resulting in a product which has a short shelf life. Since typical commercial distribution channels for antiperspirant products require storage for relatively long periods of time in factories, warehouses, and retail outlets, sometimes at elevated temperatures, degradation of the gelling agent and the resulting short product shelf life is a significant disadvantage. See, for example, U.S. Pat. No. 4,518,582, Schamper et al., issued May 21, 1985. It, therefore, would be beneficial to identify a gelling agent which forms effective hard gels in an antiperspirant context, and is stable under the acidic conditions present in such products.

The effect that various substituents have upon the hydrolysis rates of some acetals and ketals is demonstrated in Kreevoy and Taft, J. Am. Chem. Soc., 77 5590–95 (1955).

Japanese Published Application 64-62377, Kao, published Mar. 8, 1989, describes fluorinated dibenzylidene polyhydric alcohol derivatives which are effective gelling agents for cosmetic compositions containing a wide range of organic solvents. These compounds are not disclosed for use in antiperspirant compositions.

U.S. Pat. 4,429,140, Murai et al., issued Jan. 31, 1984, discloses a method for producing DBS and its derivatives. Disclosed DBS derivatives include those where the benzene ring is substituted with from 1 to 3 lower alkyl groups, lower alkoxy groups, halogen atoms or nitro groups. Para-chloro dibenzylidene xylitol and para-methoxy DBS are specifically disclosed; meta-substituted DBS derivatives are not taught. There is no suggestion to use these compounds in antiperspirant compositions.

U.S. Pat. No. 4,371,645, Mahaffey, issued Feb. 1, 1983, describes plastic compositions which include DBS derivatives for improved transparency. These DBS derivatives must include a chlorine or bromine substituent in the meta and/or para positions and may also include lower alkyl, hydroxy, methoxy, mono- or dialkyl amino, or fluorine substituents. Di(para-chloro) DBS, di(para-fluoro) DBS, and di(para-methoxy) DBS are all specifically disclosed. These compounds are not taught for use in antiperspirant compositions.

European Patent Application 0286522, Roquette Freres, published Dec. 1, 1988, describes a process for making high purity alditol diacetals. Para-chloro DBS is disclosed. However, the use of such compounds in antiperspirant compositions is not suggested.

While the art teaches some DBS-type compounds derivatized with electron withdrawing groups, there is no teaching that such compounds must be derivatized at the meta position or of using such compounds in antiperspirant stick compositions. Further, there is no suggestion that such compounds, when used in the acidic environment of an antiperspirant stick formulation, would provide effective gels and long term stability. Finally, specific compounds, such as di(meta-fluoro) DBS and di(meta-chloro) DBS, are not suggested in the art.

The present invention provides very specific gelling agents which, when used in acidic antiperspirant stick formulations, provide good gel properties without the degradation problem which typically accompanies the use of DBS in antiperspirant sticks.

SUMMARY OF THE INVENTION

The present invention provides for solid antiperspirant compositions in gel stick form, having acidic pHs, comprising:

(a) from about 0.5% to about 35% of an antiperspirant active;

(b) from about 0.5% to about 10% of a gelling agent selected from the group consisting of substituted dibenzylidene alditols (such as sorbitols, xylitols, and ribitols), and mixtures thereof, wherein at least one of the substituents on the benzene ring is selected from the group consisting of:

(1) —$CH_2F$, —$CH_2Cl$, —F, —Cl, —Br, —I, and —CH=$CHNO_2$, wherein at least one of these substituents is located at the meta position; and (2) —NO₂, —N⁺H₃, —N⁺R₃, —P⁺R₃, —P⁺H₃, —S⁺R₂, —CF₃, —CCl₃, —CHF₂, —CHCl₂, —CHClF, —CCl₂F, —CF₂Cl, —SO₃H, —SO₃R, —CO₂H, —CO₂R, —CONH₂, —CHO, —COR, and —C≡N, wherein R is C₁–C₄ alkyl and at least one of these substituents is located at the meta or para position; and (c) from about 5% to about 98% of a solvent for said gelling agent.

Preferred gelling agents are substituted dibenzylidene sorbitols, particularly those which are substituted at the meta position with fluorine or chlorine.

DETAILED DESCRIPTION OF THE INVENTION

The solid antiperspirant compositions encompassed by the present invention are in the form of gel sticks. These sticks have a suitable hardness such that they deposit an effective amount of antiperspirant material on the skin during normal use, while maintaining dimensional stability upon use and storage. Hardness of sticks can be determined by a variety of methods, including American Society for Testing and Materials (ASTM) Method D-5. This method involves the use of a needle or polished cone of particular weight and dimension, which is allowed to travel downward through the stick material for a predetermined period of time. The distance travelled by the needle or cone is a relative measure of stick hardness. Using Method D-5, with an ASTM-D1321 arrowhead-type penetration needle (Model 13-401-10, sold by Fischer Scientific Co.), weighing 50 grams, and a Model 13-399-10 Penetrometer (sold by Fischer Scientific Co.), the stick compositions of the present invention preferably have an average penetration value of from about 60 to about 200, measured in units of tenths of a millimeter, more preferably from about 100 to about 160, over a period of 5 seconds at ambient temperature. These values represent an average penetration for sticks within a given production batch, since such penetration values may vary from stick to stick within the batch.

The stick compositions of the present invention, by virtue of their incorporation of antiperspirant actives, are acidic in nature. Specifically, they have an apparent pH of from about 1.5 to about 4. The term "apparent pH" is used herein since the compositions are generally non-aqueous and, therefore, the pH of the composition is being measured in a non-aqueous system. Specifically, the pH is determined by melting the stick and measuring its pH at 25° C. using a standard pH meter. If the stick is melted at a relatively high temperature (for example, about 120° C. for about 1 hour), it will not resolidify upon cooling and the pH at 25° C. can be easily measured. Under these conditions, the apparent pH of the compositions of the present invention should be from about 1.5 to about 4.

All parts, percentages and ratios specified herein are by weight, unless otherwise specified.

The required, as well as the optional, components of the present invention are described in detail below.

Gelling Agent

The compositions of the present invention include from about 0.5% to about 10%, preferably from about 2% to about 5%, most preferably from about 2% to about 3.5%, of a specifically defined gelling agent component. This gelling agent component is a dibenzylidene alditol (for example, a sorbitol, xylitol or ribitol) substituted on the benzene ring at certain positions with one or more specific electron withdrawing groups. Dibenzylidene sorbitol (DBS) derivatives are preferred for use herein.

When the following substituents are utilized, at least one of the substituents must be located at the meta position of the benzene ring. Multiple substituents (including those not on the list) may be utilized as long as at least one from the list is located at the meta position. These substituents include: —CH₂F, —CH₂Cl, —F, —Cl, —Br, —I, and —CH=CHNO₂.

When the following substituents are utilized in the gelling agents, at least one of these substituents must be located at the meta or para position of the benzene ring. Once again, more than one of these substituents (or even substituents not on the list) may be included in a particular molecule, as long as at least one from the list is positioned at the meta or para position. These substituents include:

—NO₂, —N⁺H₃, —N⁺R₃, —P⁺R₃, —P⁺H₃, —S⁺R₂, —CF₃, —CCl₃, —CHF₂, —CHCl₂, —CHClF, —CCl₂F, —CF₂Cl, —SO₃H, —SO₃R, —CO₂H, —CO₂R, —CONH₂, —CHO, —COR, and —C≡N, wherein R is C₁–C₄ alkyl.

Preferred gelling agents for use in the present invention include the following substituents at the meta position: —CH₂F, —CH₂Cl, —F, —Cl, —Br, —I, and —CH=CHNO₂; particularly preferred are the —F and —Cl substituents. It is preferred that this meta substitution be the only substitution on the benzene ring. The substituents described herein will generally be found on both benzene rings of the compound. Particularly preferred are di(meta-fluorobenzylidene) sorbitol and di(meta-chlorobenzylidene) sorbitol, alternately referred to herein as di(meta-fluoro)DBS and di(meta-chloro)DBS, respectively.

To aid in understanding the present invention, the following are diagrams of dibenzylidene sorbitol, and dibenzylidene xylitol with the ortho, meta and para positions indicated.

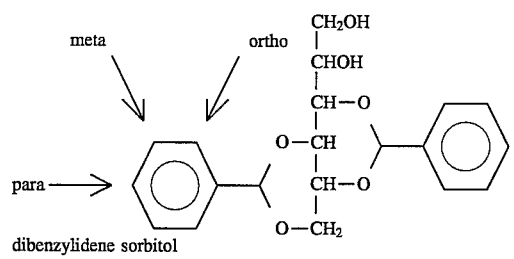
dibenzylidene sorbitol

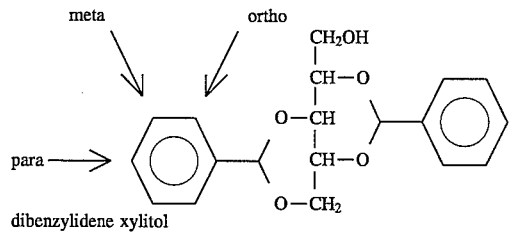
dibenzylidene xylitol

Dibenzylidene ribitol is structurally similar to dibenzylidene xylitol, except it is based on ribitol, rather than xylitol.

The structural formulas for di(meta-fluoro) DBS and di(meta-chloro) DBS are given below.

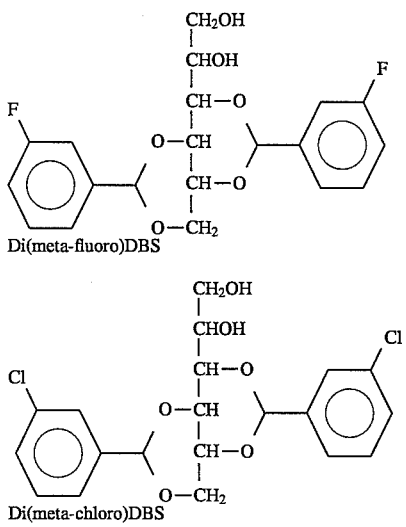

Di(meta-fluoro)DBS

Di(meta-chloro)DBS

The substituents listed above provide gelling agents which exhibit good stability in the acid environment of an antiperspirant composition. A preferred sub-group of these substituents are those which have smaller molecular sizes since they tend to generally provide stronger gels. Thus, for example, the gel provided by a fluorine or chlorine substituted compound tends to be stronger than one provided by a trifluoromethyl substituted compound. It is also preferred that the gelling agents utilized in the compositions of the present invention have a high purity. For example, they should be substantially free of para-toluene sulfonic acid or any other catalyst used in their synthesis as well as any salt forms (e.g., sodium) of these gelling agents. The presence of such impurities may tend to weaken the gel formed.

Mixtures of the gelling agents specified herein may be used in the compositions of the present invention.

In general, the gelling agents used in the present invention are formed by converting a meta-substituted benzaldehyde to the corresponding meta-substituted DBS using a reaction such as that taught in European Patent Application 0286522, Roquette Freres, published Dec. 1, 1988, incorporated herein by reference. As specific examples, the synthesis of meta-fluoro DBS and meta-chloro DBS is described below.

A solution of D-sorbitol (1006 g; 5.52 mol) in 3000 mL of distilled water, m-fluorobenzaldehyde (1240 g; 9.99 mol), and p-toluenesulfonic acid monohydrate (1310 g; 6.87 mol) is stirred at 30° C. for 21 h. The resulting suspension is neutralized to a pH of 7.0–7.5 with an aqueous 10% NaOH solution, and the white precipitate is collected by filtration. The solid is then suspended and stirred, in succession, in reagent grade acetone (3×10.0 L), and hot (60° C.) distilled water (3×10.0 L), collected, and dried in vacuo at 50° C. to give 1113 g (47%) of purified di(meta-fluoro) DBS.

Di(meta-chloro) DBS is synthesized using a similar procedure, except that meta-chloro benzyaldehyde is used in place of meta-fluoro benzaldehyde.

Para-substituted compounds used in the present invention are synthesized using a similar procedure, except that para-substituted benzaldehyde is utilized as the starting material. The general method for synthesizing substituted dibenzylidene xylitols and substituted dibenzylidene ribitols is taught in Japanese Published Application 64-62377, Kao, published Mar. 8, 1989, and U.S. Pat. No. 4,429,140, Murai et al., issued Jan. 31, 1984, both incorporated herein by reference.

Antiperspirant Active

The compositions of the present invention also contain from about 0.5% to about 35%, preferably from about 5% to about 25%, of an antiperspirant active. The antiperspirant actives hereof are antiperspirant active astringent metal salts and astringent complexes of such salts. The active may be incorporated either in solubilized or particulate form. If a clear or translucent stick composition is desired, the composition must comprise an antiperspitant active which can exist in the solvent in solubilized form. This solvent can be the same solvent used to form the base matrix with the gelling agent. Alternately, other solvents can be used as the antiperspirant active solvent in addition to the gelling agent solvent. These weight percentages are calculated on an anhydrous metal salt basis (exclusive of glycine, the salts of glycine, or other complexing agents). If used in particulate form, the material preferably has a particle size of from about 1 to about 100 microns, preferably from about 1 to about 50 microns. They may be impalpable or microspherical in form and, preferably, have a high bulk density (e.g., greater than about 0.7 g/cm$^3$). Such materials include, for example, many aluminum or zirconium astringent salts or complexes and are well known in the antiperspitant art.

Any aluminum astringent antiperspirant salt or aluminum and/or zirconium astringent complex can be employed herein. Salts useful as astringent antiperspirant salts or as components of astringent complexes include aluminum halides, aluminum hydroxyhalides, zirconyl oxyhalides, zirconyl hydroxyhalides, and mixtures of these materials.

Aluminum salts of this type include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692, Gilman, issued Jun. 3, 1975, and U.S. Pat. No. 3,904,741, Jones and Rubino, issued Sep. 9, 1975, incorporated herein by reference.

Zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2-nz is greater than or equal to 0, and B may be selected from the group consisting of halides, nitrate, sulfamate, sulfate, and mixtures thereof. Although only zirconium compounds are exemplified in this specification, it will be understood that other Group IVB metal compounds, including hafnium, can be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than 0 groups per molecule.

Several types of antiperspirant complexes utilizing the above antiperspirant salts are known in the art. For example, U.S. Pat. No. 3,792,068, Luedders et al., issued Feb. 12, 1974, discloses complexes of aluminum, zirconium and amino acids, such as glycine. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by (A) co-dissolving in water (1) one part $Al_2(OH)_{6-m}Q_m$, wherein Q is an anion selected from the group consisting of chloride, bromide and iodide, and m is a number from about 0.8 to about 2.0;

(2) x parts $ZrO(OH)_{2-a}Q_a \cdot nH_2O$, where Q is chloride, bromide or iodide; where a is from about 1 to about 2; where n is from about 1 to about 8; and where x has a value of from about 0.16 to about 1.2;

(3) p parts neutral amino acid selected from the group consisting of glycine, dl-tryptophane, dl-β-phenylalanine, dl-valine, dl-methionine and β-alanine, and where p has a value of from about 0.06 to about 0.53;

(B) co-drying the resultant mixture to a friable solid; and (C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl \cdot 2H_2O$. Preferred zirconium compounds for preparation of such ZAG-type complexes are zirconyl hydroxychloride having the empirical formula $ZrO(OH)Cl \cdot 3H_2O$ and the zirconyl hydroxyhalides of the empirical formula $ZrO(OH)_{2-a}Cl_a \cdot nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the antiperspirant complexes. See U.S. Pat. No. 4,017,599, Rubino, issued Apr. 12, 1977, incorporated herein by reference.

A wide variety of other types of antiperspirant complexes are also known in the art. For example, U.S. Pat. No. 3,903,258, Siegal, issued Sep. 2, 1975, discloses a zirconium aluminum complex prepared by reacting zirconyl chloride with aluminum hydroxide and aluminum chlorhydroxide. U.S. Pat. No. 3,979,510, Rubino, issued Sep. 7, 1976, discloses an antiperspirant complex formed from certain aluminum compounds, certain zirconium compounds, and certain complex aluminum buffers. U.S. Pat. No. 3,981,896, issued Sep. 21, 1976, discloses an antiperspirant complex prepared from an aluminum polyol compound, a zirconium compound and an organic buffer. U.S. Pat. 3,970,748, Mecca, issued Jul. 20, 1976, discloses an aluminum chlorhydroxy glycinate complex of the approximate general formula $[Al_2(OH)_4Cl][H_2CNH_2COOH]$. All of these patents are incorporated herein by reference.

Of all the above types of antiperspirant actives, preferred compounds include the 5/6 basic aluminum salts of the empirical formula $Al_2(OH)_5Cl \cdot 2H_2O$, such compounds being commonly referred to as aluminum chlorohydrates ("ACH"); mixtures of $AlCl_3 \cdot 6H_2O$ and $Al_2(OH)_5Cl \cdot 2H_2O$ with aluminum chloride to aluminum hydroxychloride weight ratios of up to about 0.5; ZAG type complexes wherein the zirconium salt is $ZrO(OH)Cl \cdot 3H_2O$, the aluminum salt is $Al_2(OH)_5Cl \cdot 2H_2O$ or the aforementioned mixtures of $AlCl_3 \cdot 6H_2O$ and $Al_2(OH)_5 Cl \cdot 2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a \cdot nH_2O$ wherein a is from about 1.5 to about 1.87 and n is from about 1 to about 7, the aluminum salt is $Al_2(OH)_5Cl \cdot 2H_2O$, and the amino acid is glycine.

Solubilized antiperspirant actives which may be utilized in the present invention are also well known in the art, and include the actives described above. Compositions containing solubilized antiperspirant active utilize solvents, such as monohydric or polyhydric alcohols or water, to solubilize the antiperspirant active before it is incorporated into the product. Examples of actives for such use are taught, for example, in U.S. Pat. No. 4,137,306, Rubino, issued Jan. 30, 1979, U.S. patent application Ser. No. 370,559, Smith and Ward, filed Jun. 23, 1989, and European Published Application 0295070, published Dec. 14, 1988, all of which are incorporated by reference herein. ACH is the preferred type of active for compositions containing solubilized antiperspirant active.

Examples of especially preferred actives include improved efficacy ACH (IACH) and improved efficacy ZAG (IZAG). The enhanced efficacy is due to improved molecular distribution. Such materials are described in U.S. Pat. No. 4,359,456, Gosling et al., issued Nov. 16, 1982; European Patent Application Publication No. 6,739, to Unilever Limited, published Jan. 9, 1980; European Patent Application Publication No. 183,171, to Armour Pharmaceutical Company, published Jun. 4, 1986; British Patent Specification No. 2,048,229, The Gillette Company, published Dec. 10, 1980; European Patent Application Publication No. 191,628, to Unilever PLC, published Aug. 20, 1986; British Patent Specification No. 2,144,992, The Gillette Company, published Mar. 20, 1985; European Patent Application Publication No. 7,191, to Unilever Limited, published Jan. 23, 1980; all incorporated by reference herein in its entirety; as well as previously incorporated U.S. Ser. No. 370,559, filed Jun. 23, 1989 and European Patent No. 0295070.

Solvent

The compositions of the present invention also include from about 5% to about 98%, preferably from about 7% to about 90%, most preferably from about 60% to about 85%, of a solvent for the gelling agent. The solvent forms the base matrix of the solid stick when combined with the gelling agent. As will be appreciated by those skilled in the art, the selection of a particular solvent will depend upon the characteristics of the stick desired. For example, the solvent can also solubilize the antiperspirant active component in formulations having solubilized antiperspirant active material. For another example, the solvent may be selected to provide such cosmetic benefits as emolliency when applied to the skin. Solvents useful herein include, for example, lower monohydric alcohols, polyhydric alcohols, and mixtures thereof. Water may be included as part of the solvent. However, the solvent will generally comprise water at levels no greater than about 5% by weight of the final composition. Sufficient non-aqueous solvent should be present to solubilize the gelling agent. Examples of solvents which may be utilized in the present invention include liquid polyethylene glycols (e.g., diethylene glycol, triethylene glycol), liquid polypropylene glycols (e.g., dipropylene glycol, tripropylene glycol), liquid polypropylene polyethylene glycol copolymers, water, ethanol, n-propanol, n-butanol, t-butanol, 2-methoxyethanol, 2-ethoxyethanol, ethylene glycol, 1,2-propylene glycol, 1,3-propylene glycol, 1,4-butylene glycol, 1,2-butylene glycol, isopropanol, isobutanol, diethylene glycol monomethylether, diethylene glycol monoethylether, 1,3-butylene glycol, 2,3-butylene glycol, 2,4-dihydroxy-2-methylpentane, trimethylene glycol, glycerine, 1,3-butane diol, 1,4-butane diol, and the like, and mixtures thereof. As used herein, polyethylene glycols, polypropylene glycols, and polypropylene polyethylene glycol copolymers include alkyl ether derivatives of these compounds (e.g., ethyl, propyl, and butyl ether derivatives). Examples of such compounds are butyl ether derivatives of polypropylene polyethylene glycol copolymers, such as PPG-5-buteth-7.

These solvents are fully described, for example, in U.S. Pat. No. 4,518,582, Schamper et al., issued May 21, 1985, and European Published Application 107,330, Luebbe et al., published May 2, 1984, incorporated herein by reference. The preferred solvents for use herein include liquid polyethylene glycols, liquid polypropylene glycols, liquid polypropylene polyethylene glycol copolymers, propylene glycol, 1,3-butylene glycol, and 2,4-dihydroxy-2-methylpentane (sometimes referred to as hexylene glycol), and mixtures thereof. Particularly preferred solvents include propylene glycol, dipropylene glycol, tripropylene glycol, triethylene glycol, hexylene glycol, and mixtures thereof.

Optional Components

The compositions of the present invention may also contain optional components which modify the physical characteristics of the compositions or serve as "active" components when deposited on the skin in addition to the antiperspirant material. Optional components useful herein are described in the following documents, all incorporated by reference herein: U.S. Pat. No. 4,049,792, Elsnau, issued Sep. 20, 1977; Canadian Patent 1,164,347, Beckmeyer et al., issued Mar. 27, 1984; European Patent Application 117,070, May, published Aug. 29, 1984; and Geria, "Formulation of Stick Antiperspirants and Deodorants", *Cosmetics & Toiletries*, 99: 55–60 (1984).

The specific non-active components that may be useful will depend upon the characteristics desired for the particular stick composition. Such components include, for example, emollients, humectants, hardeners (e.g., wax), fillers and particulate materials, colorants, perfumes, and emulsifiers. As used herein, "particulate materials" are those materials, including colloidal dispersions, that neither dissolve in the composition components nor melt during the manufacture of the stick.

The compositions of the present invention may contain from about 1% to about 40% of one or more emollients. These emollients may have an intermediate polarity, such as the ethyl, isopropyl and n-butyl diesters of adipic, phthalic and sebacic acids. Preferred examples of such emollients include di-n-butyl phthalate, diethyl sebacate, diisopropyl adipate and ethyl carbomethyl phthalate, all of which are disclosed in U.S. Pat. No. 4,045,548, Luedders et al., issued Aug. 30, 1977, which is incorporated by reference herein. Other useful emollients include $C_{12}$–$C_{15}$ alcohol benzoates (commercially available as Finsolv from Finetex, Inc.). Useful emollients also include fatty alcohols, such as cetyl and stearyl alcohols, which, if used, will be preferably present at a level of about 1% to about 10%, more preferably from about 1% to about 5%. The compositions of the present invention may also include non-polar emollients, such as volatile silicone oils, non-polar non-volatile emollients, and mixtures thereof. The term "volatile", as used herein, refers to those materials which have a measurable vapor pressure at ambient temperature.

Volatile silicone oils useful in the cosmetic stick compositions of the present invention are preferably cyclic or linear polydimethylsiloxanes containing from about 3 to about 9, preferably from about 4 to about 5, silicon atoms. The following formula illustrates cyclic volatile polydimethylsiloxanes useful in the antiperspirant stick compositions disclosed herein:

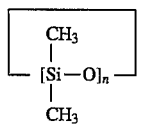

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes at 25° C., while cyclic materials typically have viscosities of less than about 10 centistokes. A description of various volatile silicone oils is found in Todd et al., "Volatile Silicone Fluids for Cosmetics", *Cosmetic & Toiletries*, 91, pages 27–32 (1976), the disclosures of which are incorporated by reference herein.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by Union Carbide Corp.); SF 1202 (manufactured by General Electric); and SWS-03314 (manufactured by SWS Silicones, Inc.).

Non-volatile silicone oils useful as emollient materials include polyalkylsiloxanes, polyarylsiloxanes and polyethersiloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 2 to about 400 centistokes at 25° C. Such polyalkyl siloxanes include the Viscasil series (sold by General Electric Company) and the Dow Corning 200 series (sold by Dow Corning Corp.). Polyalkylaryl siloxanes include polymethylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corp.). Useful polyether siloxane copolymers include, for example, a polyoxyalkylene ether copolymer having a viscosity of about 1200 to 1500 centistokes at 25° C. Such a fluid is available as SF1066 organosilicone surfactant (sold by General Electric Company). Polysiloxane ethylene glycol ether copolymers are preferred copolymers for use in the present compositions.

The compositions of the present invention may contain a processing aid. These components, which are generally used within the range of about 1% to about 25%, of the composition, act to reduce the gel formation temperature of the composition or reduce the melting temperature of the gellant. Examples of such materials are taught in U.S. Pat. No. 4,719,102, Randhawa et al., issued Jan. 12, 1988, incorporated herein by reference, and include, among others, propylene carbonate, butyrolactone, caprolactone, and mixtures thereof. More preferred processing aids are cosolvents, used in combination with the solvents described above (e.g., monohydric and polyhydric alcohols), which are 2-oxazolidinone compounds having a $C_1$–$C_4$ alkyl radical substituted at the 3 position of the heterocyclic ring, or a mixture of such compounds. This cosolvent should be miscible with the solvent. The gelling agent should be more soluble in the cosolvent than in said other solvent in order for processing temperature of the compositions to be reduced. The 2-oxazolidinone cosolvent will typically be present in the composition at a level of about 0.5% to about 40%, by weight, of the composition, preferably from about 1% to about 25%, more preferably from about 5% to about 15%. The weight ratio of monohydric and polyhydric alcohol solvent to said 2-oxazolidinone is preferably from about 1:1 to about 50:1, more preferably from about 3:1 to about 20:1, and a weight ratio of gelling agent to said 2-oxazolidinone is preferably from about 0.05:1 to about 2:1, more preferably from about 0.1:1 to about 1:1.

In general the 2-oxazolidinone compound has the formula:

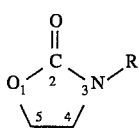

wherein the radical R at the 3 position is a $C_1$–$C_4$ alkyl, preferably a $C_1$–$C_2$ alkyl, more preferably $C_1$ (i.e., methyl). The preferred compounds have hydrogen at the 4 and 5 positions, and are identified as 3-($C_1$–$C_4$ alkyl)-2-oxazolidinones. Most preferred is 3-methyl-2-oxazolidinone. The compound may have substituents located at the 4 and 5 positions of the heterocyclic ring instead of hydrogen. Preferably, if used, such substituents are lower chain alkyls, e.g., $C_1$–$C_4$ alkyl, preferably $C_1$–$C_2$ alkyl, more preferably methyl. Other substituents can be present which do not cause the compound to be immiscible with other solvents or reduce solubility of the gelling agent in it to less than in the mono- and polyhydric alcohol solvent. Also, the compound should remain stable against decomposition in the processing of and under the typical storage and use conditions of the gel stick compositions. The compositions may also include a stabilizing agent which acts to stabilize the composition (especially the gelling agent) during the high temperature steps of the manufacturing process, or during storage, or both. Examples of these material include zinc acetate, methenamine, magnesium acetate, calcium acetate, triethanolamine, diethanolamine, and mixtures thereof. Preferred stabilizing agents are $C_4$–$C_6$ (saturated) dicarboxylates, $C_6$–$C_8$ (saturated) monocarboxylates, and substituted and unsubstituted benzoates. These will be added as salts which are at least partially soluble in the solvent system. Suitable salt-forming cations include sodium, potassium, lithium, magnesium, calcium, and zinc. Preferred salt-forming cations are sodium, potassium, magnesium, and calcium, especially sodium. Especially preferred stabilizing agents include the unsubstituted benzoates, succinate, and octanoate salts, particularly the sodium and potassium salts thereof.

The compositions of the present invention may also contain from about 0.5% to about 10% of an inert filler material. Suitable filler materials include colloidal silica (such as Cab-O-Sil, sold by Cabot Corp.), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in cosmetic sticks is disclosed in U.S. Pat. No. 4,126,679, Davy et al., issued Nov. 21, 1987, incorporated herein by reference. The compositions of the present invention may also include perfumes, emulsifiers and coloring agents well known in the art, at levels of from about 0.1% to about 5%.

In addition to the antiperspirant actives, discussed above, the antiperspirant sticks of the present invention may also contain a safe and effective amount of one or more additional components which are meant to be deposited upon human tissue. Such active components include astringents, bacteriostats, fungistats, pigments, dyes, colorants, perfumes, emollients, ultraviolet absorbers, and mixtures thereof. These components must be stable in the formulation of the instant invention. A "safe and effective" amount of such active components is that amount which yields the desired benefit at a reasonable benefit/risk ratio for human usage. Various active components among those useful in the present invention are described in U.S. Pat. No. 4,226,889, Yuhas, issued Oct. 7, 1980, incorporated by reference herein.

The compositions of this invention may be made by methods known to those skilled in the art. Such methods are described in "Gels and Sticks Formulary", *Cosmetics & Toiletries*, 99, 77–84 (1984), incorporated by reference herein. Such methods generally involve admixture of the DBS-derivative gelling agent to a solvent upon heating to a temperature sufficient to dissolve the gelling agent. Such temperature is generally from about 110° C. to about 135° C. The antiperspirant active and optional components are then added and the solution is poured into stick molds. A solid gel forms upon cooling. As the stick composition may solidify rapidly upon cooling, care should be taken so as to maintain an elevated temperature while mixing and processing the composition.

The gel form antiperspirant stick compositions of the present invention are used in a conventional manner. Specifically, the compositions may be used to prevent and/or control perspiration wetness by topically applying, one or more times a day, an effective amount of the composition to areas of the body particularly prone to perspiration (e.g., the underarm or axillary area).

The following non-limiting examples illustrate the compositions, methods of making, and methods of use described in the present application.

EXAMPLES I–VII

Opaque antiperspirant gel stick compositions (i.e., gel stick compositions containing antiperspirant active in particulate form) of the present invention, having the formulas given below, are made by the following procedure.

Phase A—Weigh the required amount of each solvent into a 3-neck round bottom flask containing a stir bar. Place the flask in a heating mantle connected to a rheostat.

Weigh the required amount of gellant and add it to the solvents in the flask. Connect a water-cooled condenser to one neck of the flask, place a thermometer in another neck and cover the 3rd neck with a stopper.

Heat the flask while stirring the contents until the gellant is completely solubilized (usually 110° C.–132° C.).

Add the clay and silica to the gellant solution. Remove the flask from the heating mantle but continue stirring the mixture. When the temperature of the mixture drops down to 102° C.±3° C., add phase B to this mixture. Stir for no longer than 3 minutes then transfer into canisters (cover each canister loosely). Allow to cool to room temperature.

Phase B—Weigh the glycol solvent into a beaker containing a mechanical stirrer and heat to about 55° C. to about 60° C. Add an equal amount of powdered antiperspirant active, stir, and add to phase A.

These antiperspirant stick compositions have an apparent pH of about 2.5.

| Ingredients | Examples | | |
|---|---|---|---|
| | I | II | III |
| Phase A | | | |
| Dipropylene glycol | 31.90 | 36.72 | 36.61 |
| Hexylene glycol | 20.03 | — | — |
| PPG-5-Buteth-7 | — | 19.91 | — |
| Tripropylene glycol | — | — | 19.81 |
| Propylene carbonate | 7.98 | 8.13 | 7.97 |
| Finsolv TN | 4.99 | — | — |
| Di(meta-fluoro)DBS | 2.50 | 2.50 | 2.48 |
| Bentone 38[1] | 1.50 | 1.49 | 1.49 |
| Cabosil[3] | 1.00 | 1.00 | 1.00 |
| Phase B | | | |
| I-ACH[2]/Propylene glycol (50/50) | 30.10 | 30.25 | — |
| I-ACH/PEG-8 (50/50) | — | — | 30.64 |

[1]Commercially available from N L Industries.
[2]Commercially available from Westwood Chemical Corp.
[3]Commercially available from Cabot Corp.

Substantially similar results are obtained when the di(meta-fluoro) DBS is replaced, in whole or in part, by an equivalent amount of di(meta-chloro) DBS.

The opaque sticks are storage stable and provide excellent antiperspirant efficacy when applied to the axillary area.

Clear antiperspirant gel stick compositions (i.e., gel stick compositions containing antiperspirant active in solubilized form) of the present invention, having the formulas given below, are made by the following procedure.

Phase A—Weigh the required amount of each solvent into a 3-neck round bottom flask containing a stir bar. Place the flask in a heating mantle connected to a rheostat.

Weigh the required amount of gellant and add it to the solvents in the flask. Connect a water-cooled condenser to one neck of the flask, place a thermometer in another neck and cover the 3rd neck with a stopper.

Heat the flask while stirring the contents until all the gellant dissolves (usually 110° C.–132° C.). After the gellant is completely solubilized, take the flask out of the heating mantle but continue stirring the solution. When the solution temperature drops down to 94° C.±3° C., add phase B to it, stir for 2–3 min., but not more than about 5 min. Transfer the mixture into canisters and cover loosely. Allow to cool to room temperature.

Phase B—Dissolve the antiperspirant active in propylene glycol (PG) and water ($H_2O$) such that the resulting mixture is 50/46/4 I-ACH/PG/$H_2O$. Heat this mixture in a 3-neck round bottom flask using the same setup as phase A. Maintain the temperature at 55°–60° C.

These antiperspirant stick compositions have an apparent pH of between about 1.5 and about 4.

| Ingredients | Examples | | | |
|---|---|---|---|---|
| | IV | V | VI | VII |
| Phase A | | | | |
| Tripropylene glycol | — | — | 6.50 | — |
| Dipropylene glycol | 34.36 | 33.97 | 29.95 | 29.40 |
| Hexylene glycol | — | 20.00 | — | — |
| PPG-5-buteth-7[1] | 24.85 | — | 20.00 | 19.90 |
| Propylene carbonate | 8.02 | 8.01 | 8.10 | 7.97 |
| Finsolv TN | — | 5.00 | — | — |
| PEG 400 | — | — | 3.12 | 10.03 |
| Di(meta-fluoro)DBS | 2.51 | 3.02 | 2.51 | 2.52 |
| Phase B | | | | |
| I-ACH[2] | 15.13 | 15.00 | 14.91 | 15.09 |
| Propylene glycol | 13.93 | 13.80 | 13.71 | 13.89 |
| Water | 1.20 | 1.20 | 1.20 | 1.20 |

[1]Commercially available from Union Carbide.
[2]Commercially available from Westwood Chemical Corp.

Substantially similar results are obtained when the d(meta-fluoro) DBS is replaced, in whole or in part, by an equivalent amount of di(meta-chloro) DBS.

The clear sticks are storage stable and provide excellent antiperspirant efficacy when applied to the axillary area.

EXAMPLE VIII

Another opaque antiperspirant gel stick composition is exemplified in this example. The composition is made according to the following procedure.

Phase A—Weigh the water into a beaker. Add the sodium benzoate and agitate at room temperature until the sodium benzoate is dissolved, to form a sodium benzoate solution.
Add the sodium benzoate solution, the Phase A portion of the dipropylene glycol, propylene glycol, and 3-methyl-2-oxazolidinone into a 3-neck round bottom flask equipped with a reflux condenser, thermometer, and magnetic stir bar. Place the flask in a heating mantle connected to a rheostat.
Weigh the gelling agent and add it to the flask. Heat the flask while stirring until the gelling agent is completely dissolved at about 110° C. to about 132° C. Hold at about 110° C.–132° C. with stirring.

Phase B—Weigh the Phase B portion of the dipropylene glycol and ethanol into a round bottom flask equipped with a reflux condenser, thermometer, and mechanical stirrer. Add the antiperspirant active and mix until well dispersed. Mixing can alternately be performed with a high shear mixer. Add the fumed silica and fumed aluminum oxide to the flask, place the flask in a heating mantle connected to a rheostat, and heat the flask to about 65° C. to about 90° C. while stirring. Hold at about 65° C.–90° C. with stirring.
Add Phase B to Phase A flask and mix until homogenous. Pour the liquid mixture into canister(s) and cover loosely to contain volatile materials. Allow composition to cool to room temperature to form the gel.

| Ingredients | Weight % |
|---|---|
| Phase A | |
| Sodium Benzoate | 1.00 |
| Water | 2.00 |
| Dipropylene Glycol | 15.00 |
| Propylene Glycol | 15.00 |
| 3-Methyl-2-Oxazolidinone | 10.00 |
| Di(m-fluorobenzylidene) Sorbitol | 3.00 |
| Phase B | |
| Dipropylene Glycol | 27.00 |
| Ethanol | 10.00 |

15
-continued

| Ingredients | Weight % |
| --- | --- |
| Zirconium Aluminum Trichlorohydrex Gly (ZAG)* | 15.00 |
| Fumed Silica** | 1.67 |
| Fumed Aluminum Oxide*** | 0.30 |

*Avaiable as WESTCHLOR ZR 30B DM Powder from Westwood Chemical Corp. (Middletown, NY, USA).
**Available as CABOSIL from Cabot Corp. (Tuscola, IL, USA).
***Available as ALuminum Oxide C from Degussa, Inc. (Teterboro, NJ, USA).

EXAMPLE IX

A clear antiperspirant gel stick composition is exemplified in this example. The composition is made according to the following procedure.

Phase A—Weigh the Phase A portion of the water into a beaker. Add the sodium benzoate and agitate at room temperature until the sodium benzoate is dissolved, to form a sodium benzoate solution.

Add the sodium benzoate solution, the dipropylene glycol, and the 3-methyl-2-oxazolidinone into a 3-neck round bottom flask equipped with a reflux condenser, thermometer, and magnetic stir bar. Place the flask in a heating mantle connected to a rheostat.

Weigh the gelling agent and add it to the flask. Heat the flask while stirring until the gelling agent is completely dissolved at about 110° C. to about 132° C. Hold at about 110° C.–132° C. with stirring.

Phase B—Weigh the propylene glycol into a flask. Add the antiperspirant active and mix until homogenous. Add the Phase B portion of the water. Mix with a high energy mixer and heat to about 45° C. to about 85° C. while mixing until the active is solubilized. Deaerate as appropriate.

Add solubilized active, ethanol, and silica into a round bottom flask equipped with a reflux condenser, thermometer, and magnetic stir bar. Place the flask in a heating mantle connected to a rheostat, and heat the flask to about 65° C. to about 90° C. while stirring. Hold at about 65° C.–90° C. with stirring.

Add Phase B to Phase A flask and mix until homogenous. Pour the liquid mixture into canister(s) and cover loosely to contain volatile materials. Allow composition to cool to room temperature to form the gel. The composition will be clear or translucent.

| Ingredients | Weight % |
| --- | --- |
| Phase A | |
| Sodium Benzoate | 1.00 |
| Water | 2.00 |
| Dipropylene Glycol | 43.00 |
| 3-Methyl-2-Oxazolidinone | 10.00 |
| Di(m-fluorobenzylidene) Sorbitol | 3.00 |
| Phase B | |
| Ethanol | 10.00 |
| Propylene Glycol | 15.00 |
| Aluminum Chlorohydrate* | 13.50 |
| Fumed Silica** | 1.00 |
| Water | 1.50 |

*Available as WESTCHLOR DM 200 Powder from Westwood Chemical Corp. (Middletown, NY, USA).
**Available as CABOSIL from Cabot Corp. (Tuscola, IL, USA).

What is claimed is:

1. A solid antiperspirant composition in gel stick form, having an acidic pH, comprising:
   (a) from about 0.5% to about 35% of an antiperspirant active;
   (b) from about 0.5% to about 10% of a gelling agent selected from the group consisting of substituted dibenzylidene alditols, and mixtures thereof, wherein at least one of the substituents on the benzene ring is selected from the group consisting of:
      (1) $-CH_2F$, $-CH_2Cl$, $-F$, $-Cl$, $-Br$, $-I$, and $-CH=CHNO_2$, wherein at least one of these substituents is located at the meta position; and
      (2) $-NO_2$, $-N^+H_3$, $-N^+R_3$, $-P^+R_3$, $-P^+H_3$, $-S^+R_2$, $-CF_3$, $-CCl_3$, $-CHF_2$, $-CHCl_2$, $-CHClF$, $-CCl_2F$, $-CF_2Cl$, $-SO_3H$, $-SO_3R$, $-CO_2H$, $-CO_2R$, $-CONH_2$, $-CHO$, $-COR$, and $-C\equiv N$, wherein R is $C_1$–$C_4$ alkyl and at least one of these substituents is located at the meta or para position; and
   (c) from about 5% to about 98% of a solvent for said gelling agent.

2. A solid antiperspirant composition according to claim 1 wherein the substituted dibenzylidene alditol is selected from the group consisting of substituted dibenzylidene sorbitols, substituted dibenzylidene xylitols, substituted dibenzylidene ribitols, and mixtures thereof.

3. A solid antiperspirant composition according to claim 2 wherein the gelling agent is a substituted dibenzylidene sorbitol.

4. A solid antiperspirant composition according to claim 3 wherein, in the gelling agent, at least one of the substituents on the benzene ring is selected from the group consisting of $-CH_2F$, $-CH_2Cl$, $-F$, $-Cl$, $-Br$, $-I$, and $-CH=CHNO_2$, and at least one of these substituents is located at the meta position.

5. A solid antiperspirant composition according to claim 4 wherein, in the gelling agent, the sole substituent on the benzene ring is selected from the group consisting of $-F$ and $-Cl$.

6. A solid antiperspirant composition according to claim 5 wherein the gelling agent is di(meta-fluorobenzylidene) sorbitol.

7. A solid antiperspirant composition according to claim 5 wherein the gelling agent is present at from about 2% to about 5%.

8. A solid antiperspirant composition according to claim 4 having an apparent pH of from about 1.5 to about 4.

9. A solid antiperspirant composition according to claim 4 wherein the solvent is selected from the group consisting of liquid polyethylene glycols, liquid polypropylene glycols, liquid polyethylene polypropylene glycol copolymers, water, ethanol, n-propanol, n-butanol, t-butanol, 2-methoxyethanol, 2-ethoxyethanol, ethylene glycol, 1,2-propylene glycol, 1,3-propylene glycol, 1,4-butylene glycol, 1,2-butylene glycol, isopropanol, isobutanol, diethylene glycol monomethylether, diethylene glycol monoethylether, 1,3-butylene glycol, 2,3-butylene glycol, 2,4-dihydroxy-2-methylpentane, trimethylene glycol, glycerine, 1,3-butane diol, 1,4-butane diol, and mixtures thereof.

10. A solid antiperspirant composition according to claim 9 wherein the solvent is present at from about 7% to about 90%.

11. A solid antiperspirant composition according to claim 9 wherein the antiperspirant active has the formula $Al_2(OH)_xQ_y \cdot XH_2O$, where Q is selected from the group consisting of chlorine, bromine and iodine, x is from about 2 to about 5, x+y=about 6, and x and y do not need to be integers, and X is from about 1 to about 6.

12. A solid antiperspirant composition according to claim 7 wherein the gelling agent is present at from about 2% to about 3.5%.

13. A solid antiperspirant composition according to claim 9 wherein the solvent comprises a material selected from the group consisting of propylene glycol, dipropylene glycol, tripropylene glycol, triethylene glycol, hexylene glycol, and mixtures thereof.

14. A solid antiperspirant composition according to claim 1 wherein the antiperspirant active is in solubilized form.

15. A solid antiperspirant composition according to claim 4 wherein the antiperspirant active is in solubilized form.

16. A solid antiperspirant composition according to claim 15 wherein said solvent comprises material selected from the group consisting of polyhydric alcohols, and mixtures thereof.

17. A solid antiperspirant composition according to claim 16, wherein said antiperspirant active comprises an aluminum chlorohydrate.

18. A solid antiperspirant composition according to claim 1 wherein the antiperspirant active is in particulate form.

19. A solid antiperspirant composition according to claim 4 wherein the antiperspirant active is in particulate form.

20. A solid antiperspirant composition according to claim 19 wherein said solvent comprises material selected from the group consisting of polyhydric alcohols, and mixtures thereof.

21. A solid antiperspirant composition according to claim 20, wherein said antiperspirant active comprises an aluminum chlorohydrate, a zirconium-aluminum-glycine complex or a mixture thereof.

22. A method for preventing and controlling perspiration wetness in humans comprising the application to the underarm area of an effective amount of the solid antiperspirant composition according to claim 1.

* * * * *